(12) United States Patent
Tran

(10) Patent No.: US 11,174,980 B1
(45) Date of Patent: Nov. 16, 2021

(54) DUAL TELESCOPIC POINTER WITH ADJUSTABLE BALL JOINTS

(71) Applicant: Amber Tran, Gold River, CA (US)

(72) Inventor: Amber Tran, Gold River, CA (US)

( * ) Notice: Subject to any disclaimer, the term of this patent is extended or adjusted under 35 U.S.C. 154(b) by 0 days.

(21) Appl. No.: 17/065,430

(22) Filed: Oct. 7, 2020

(51) Int. Cl.
*F16M 11/14* (2006.01)
*G09B 17/02* (2006.01)
*A61H 5/00* (2006.01)

(52) U.S. Cl.
CPC ............... *F16M 11/14* (2013.01); *A61H 5/00* (2013.01); *G09B 17/02* (2013.01)

(58) Field of Classification Search
CPC ........... F16M 11/14; A61H 5/00; G09B 17/02
See application file for complete search history.

(56) References Cited

U.S. PATENT DOCUMENTS

2017/0366746 A1* 12/2017 Yu ......................... F16M 11/041
2018/0112820 A1* 4/2018 Lau ........................ F16M 11/14
2019/0120423 A1* 4/2019 Couch, III ............. F16M 13/02

FOREIGN PATENT DOCUMENTS

CN 207895732 U * 9/2018

OTHER PUBLICATIONS

David Grand: "Brainspotting: The Revolutionary New Therapy for Rapid and Effective Change" Published Apr. 1, 2013, Publisher: Sounds True, pp. 179 (Year: 2013).*
Sandao telescopic pointer sold on amazon.com first available date Nov. 4, 2018, weblink https://www.amazon.com/Telescopic-Extendable-Retractable-Presenter-Whiteboard/dp/B07K5W2DTZ (Year: 2018).*

* cited by examiner

*Primary Examiner* — Eret C McNichols
*Assistant Examiner* — Ding Y Tan
(74) *Attorney, Agent, or Firm* — Craig A. Simmermon

(57) ABSTRACT

Dual telescopic pointer with adjustable ball joints is used by a trained clinician to help treat a client or patient with a mental illness. The trained clinician places a dual telescopic pointer with adjustable ball joints in front of a client and then counseling or analyzing the client in the usual fashion while also asking the client to focus their eyes and attention on the first or second focus spheres of the dual telescopic pointer with adjustable ball joints while periodically moving the location of the first or second focus spheres by extending and/or retracting the first and second telescopic pointers which support the first or second focus spheres respectively and/or adjusting the first or second adjustable ball joints which support the first and second telescopic pointers respectively. This method of treatment promotes deeper healing in the subcortical areas of the brain where emotions and trauma are stored.

3 Claims, 8 Drawing Sheets

DUAL TELESCOPIC POINTER WITH ADJUSTABLE BALL JOINTS

BACKGROUND OF THE INVENTION

1. Field of the Invention

This invention relates to a telescopic pointer and more specifically to a device with two telescopic pointers that are each attached to an adjustable ball joint that is attached to a stable base with optional casters or wheels on the bottom of the stable base.

2. Description of Related Art

There are other telescopic pointers in the prior art however there are none with two telescopic pointers that are each attached to an adjustable ball joint that is attached to a stable base with optional casters or wheels on the bottom of the stable base as shown and described below.

The dual telescopic pointer with adjustable ball joints of this invention is used during a mental health treatment approach called "Brainspotting" with a trained clinician and client. Brainspotting theory holds that is the location of a person's focus affects how he or she feels. After the targeted issue has been determined, the telescopic pointer is adjusted depending on the need of the client and the issue being processed. This may include adjustment horizontally, vertically, closer, or further from the client. Once a position is decided, the client is asked to focus on one end of either telescopic pointer to access memories, thoughts, feelings, and bodily sensations associated with the issues. This method of processing promotes deeper healing in the sub-cortical areas of the brain where emotions and trauma are stored. Brainspotting is an established and recognized mental health treatment approach within the field of psychological analysis.

BRIEF SUMMARY OF THE INVENTION

It is an aspect of dual telescopic pointer with adjustable ball joints to include two telescopic pointers.

It is an aspect each telescopic pointer to be extendable and retractable.

It is an aspect each telescopic pointer to include a focus sphere that attracts the attention or focus of a client.

It is an aspect of each telescopic pointer to be reversibly rigidly attachable to an adjustable ball joint.

It is an aspect of each adjustable ball joint to be adjusted or pointed in any direction and then tightened to rigidly remain in the adjusted position.

It is an aspect of each adjustable ball joint adjustably point or direct a telescopic pointer in any direction.

It is an aspect of each adjustable ball joint to be reversibly rigidly attachable to the upper side of a rigid base.

It is an aspect of dual telescopic pointer with adjustable ball joints to adjustably point or direct two focus spheres in any direction and then rigidly hold the two focus spheres in the adjusted position.

It is an optional aspect of dual telescopic pointer with adjustable ball joints to have a plurality of casters or wheels rigidly attached to the lower side of rigid base.

DEFINITION LIST

Figure 1:
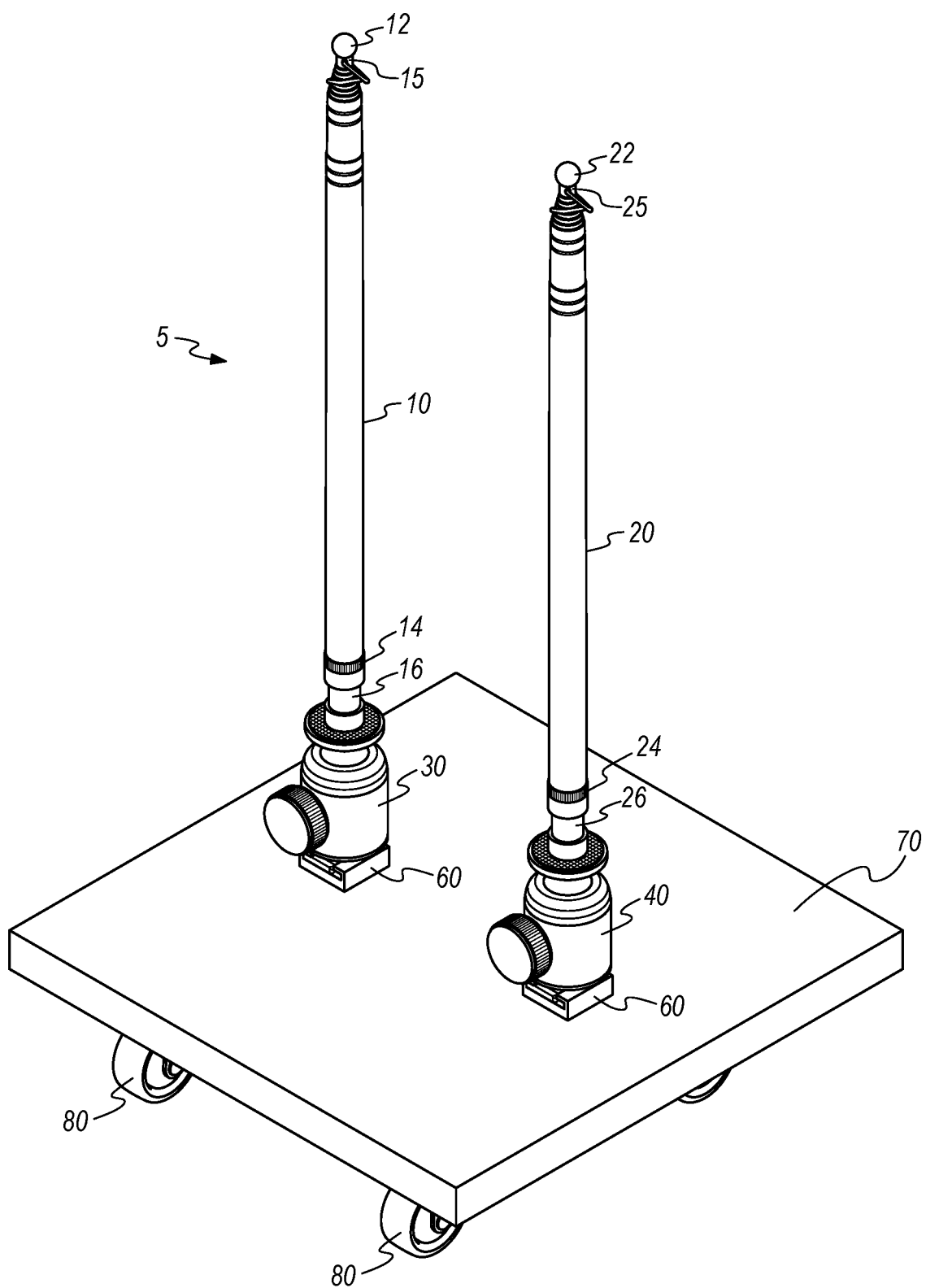
FIG. 1 is a top perspective view of dual telescopic pointer with adjustable ball joints with both telescopic pointers in the retracted position.
Figure 2:
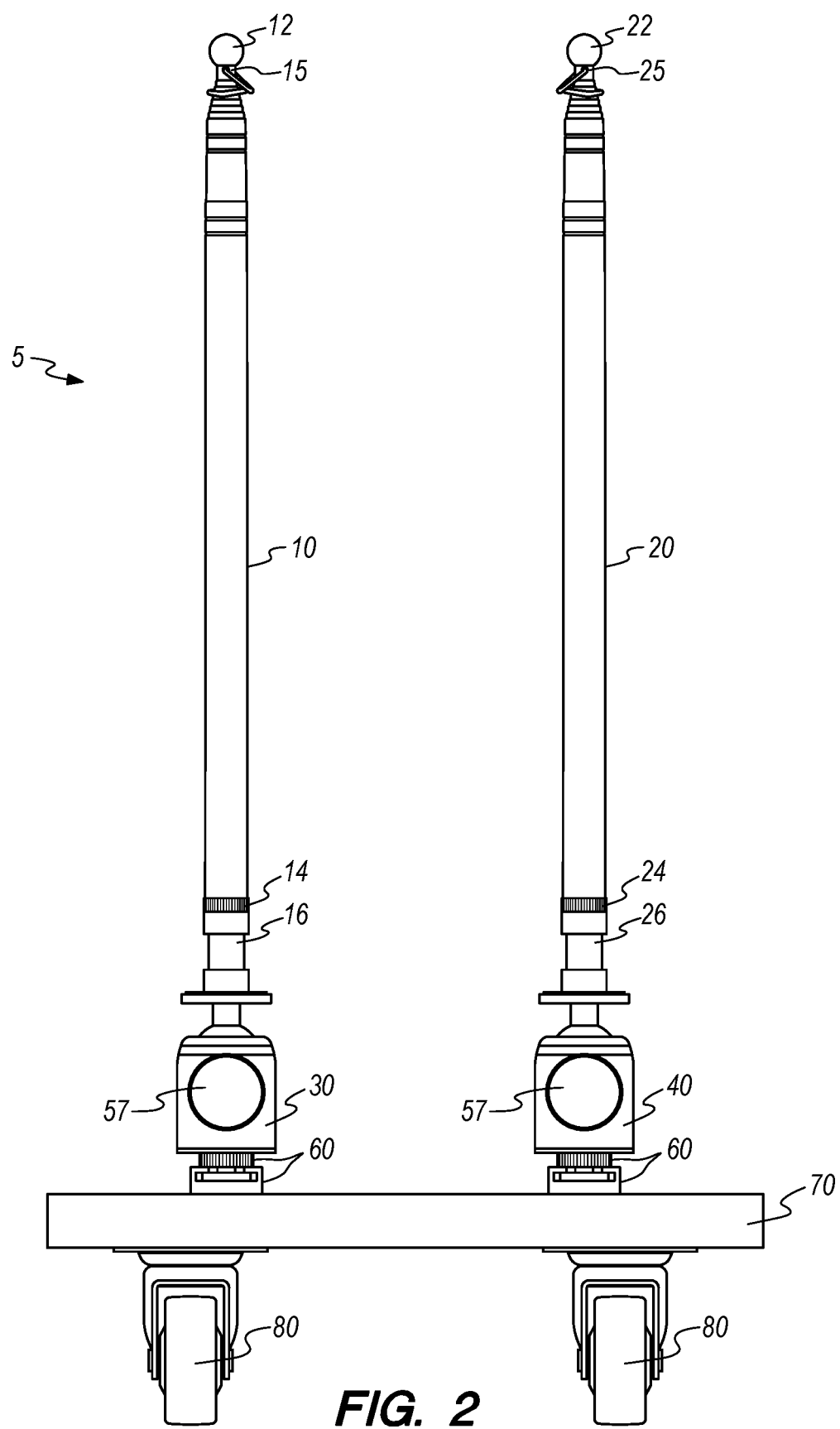
FIG. 2 is a front elevation view of dual telescopic pointer with adjustable ball joints with both telescopic pointers in the retracted position.
Figure 3:
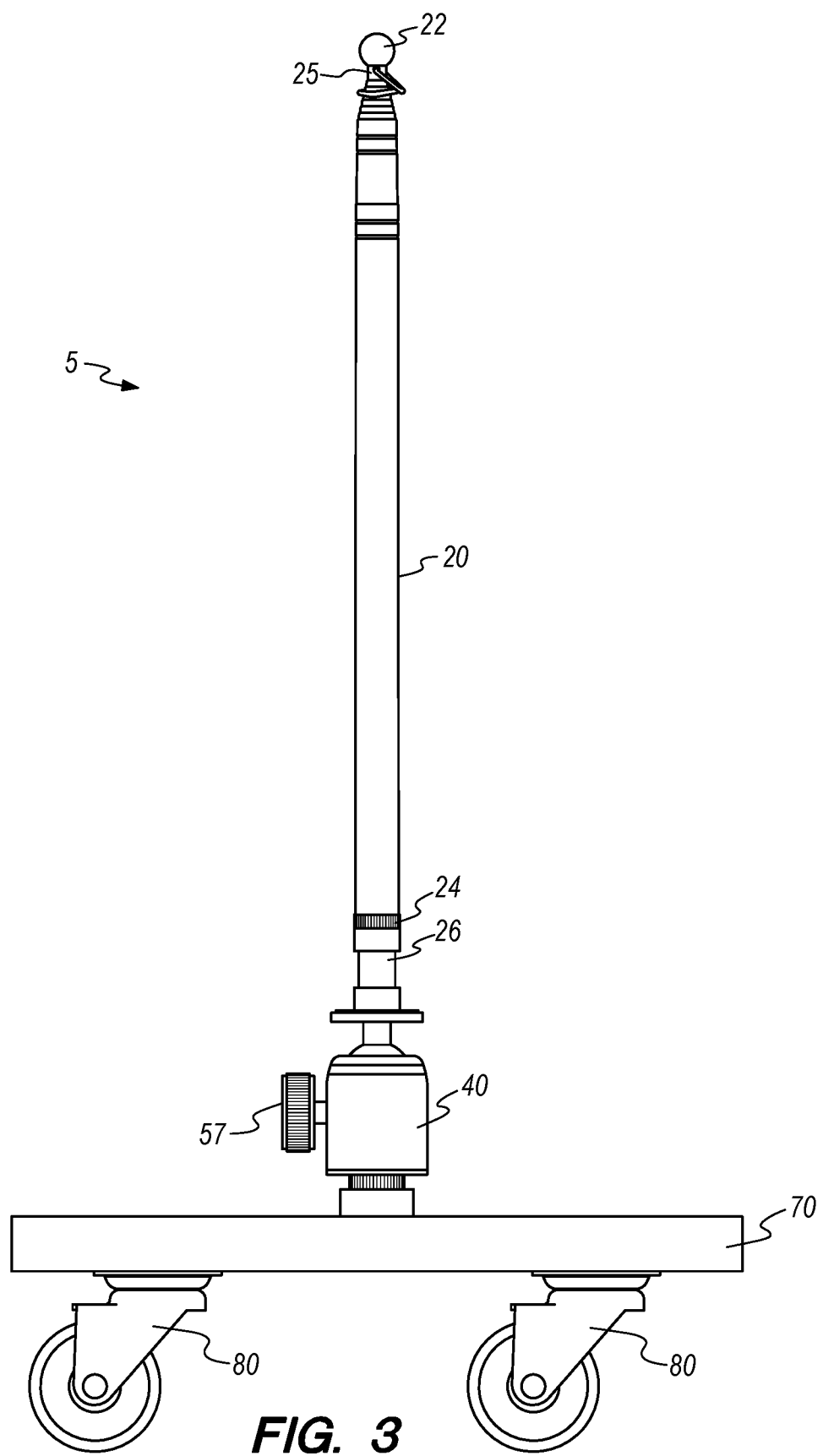
FIG. 3 is a right side elevation view of dual telescopic pointer with adjustable ball joints with both telescopic pointers in the retracted position.
Figure 4:
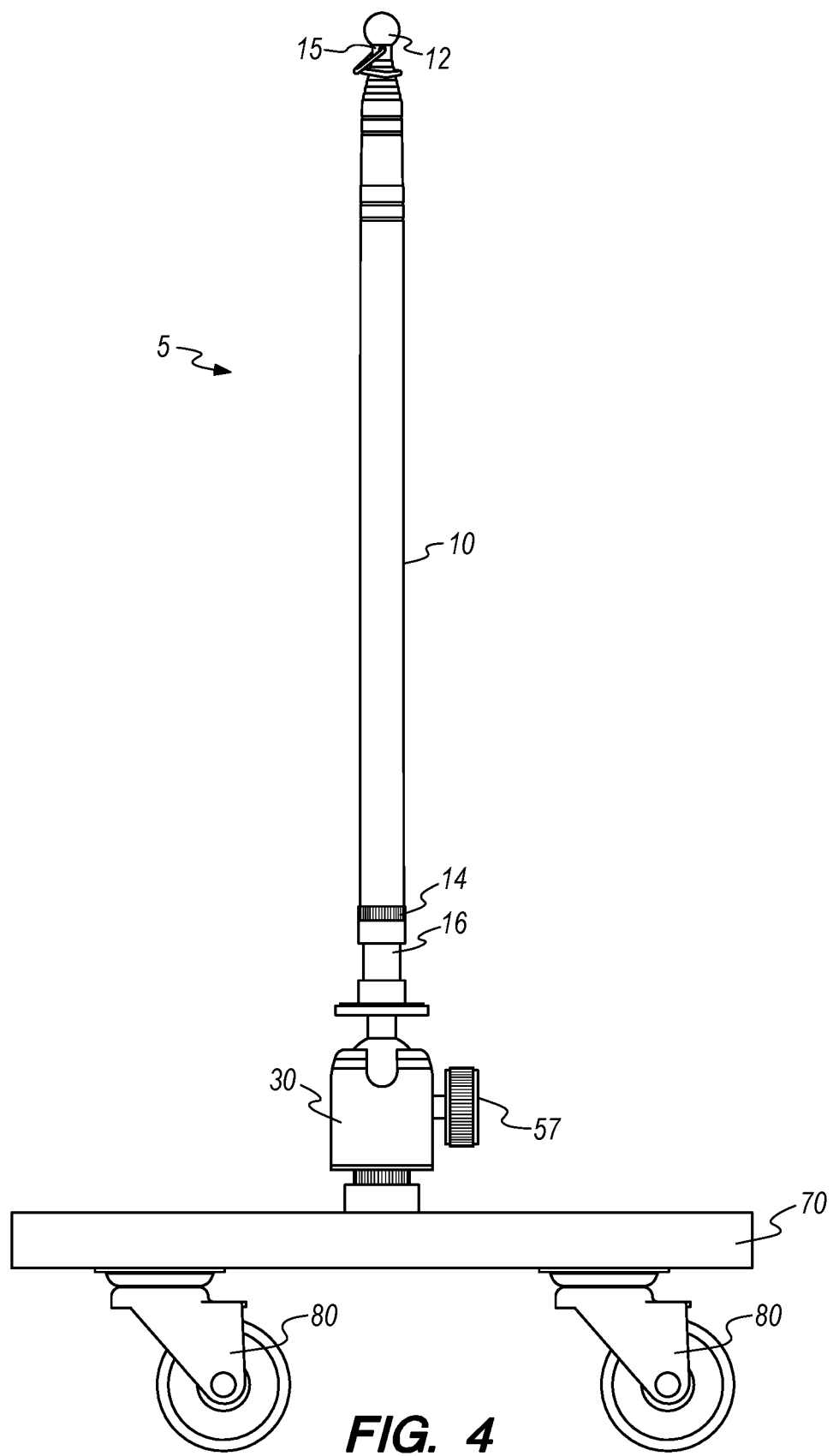
FIG. 4 is a left side elevation view of dual telescopic pointer with adjustable ball joints with both telescopic pointers in the retracted position.
Figure 5:
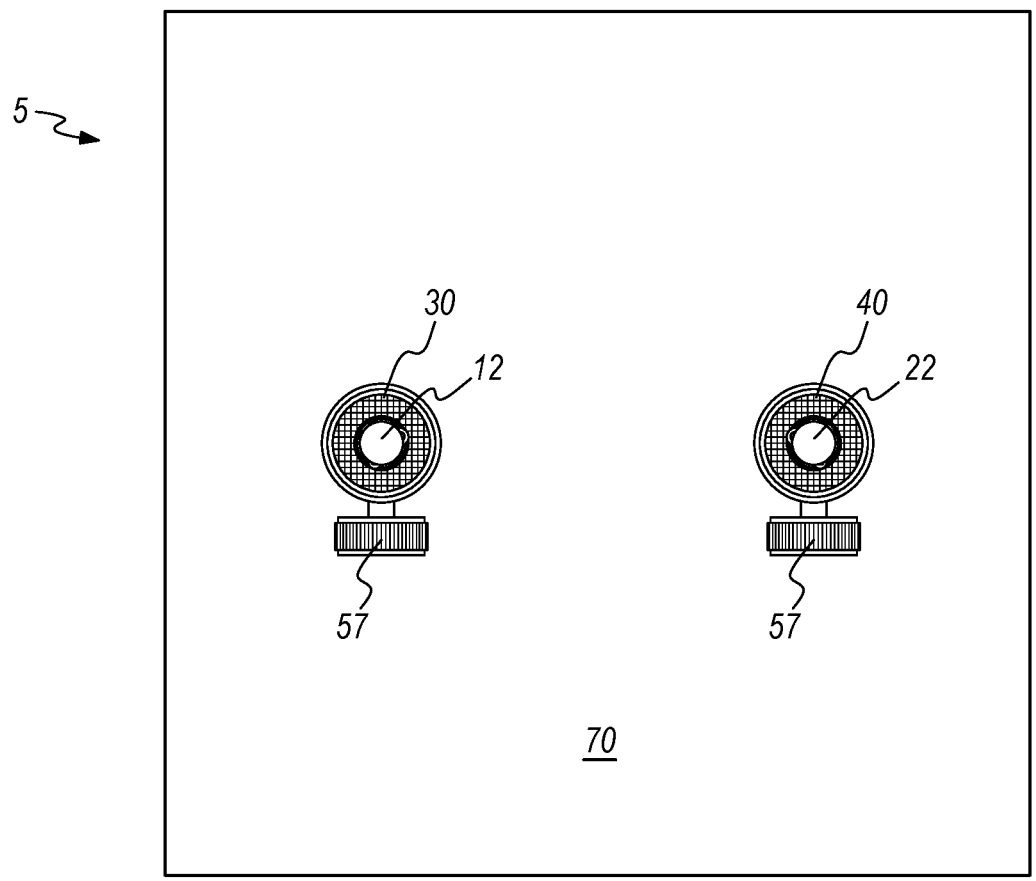
FIG. 5 is a top plan view of dual telescopic pointer with adjustable ball joints with both telescopic pointers in the retracted position.
Figure 6:
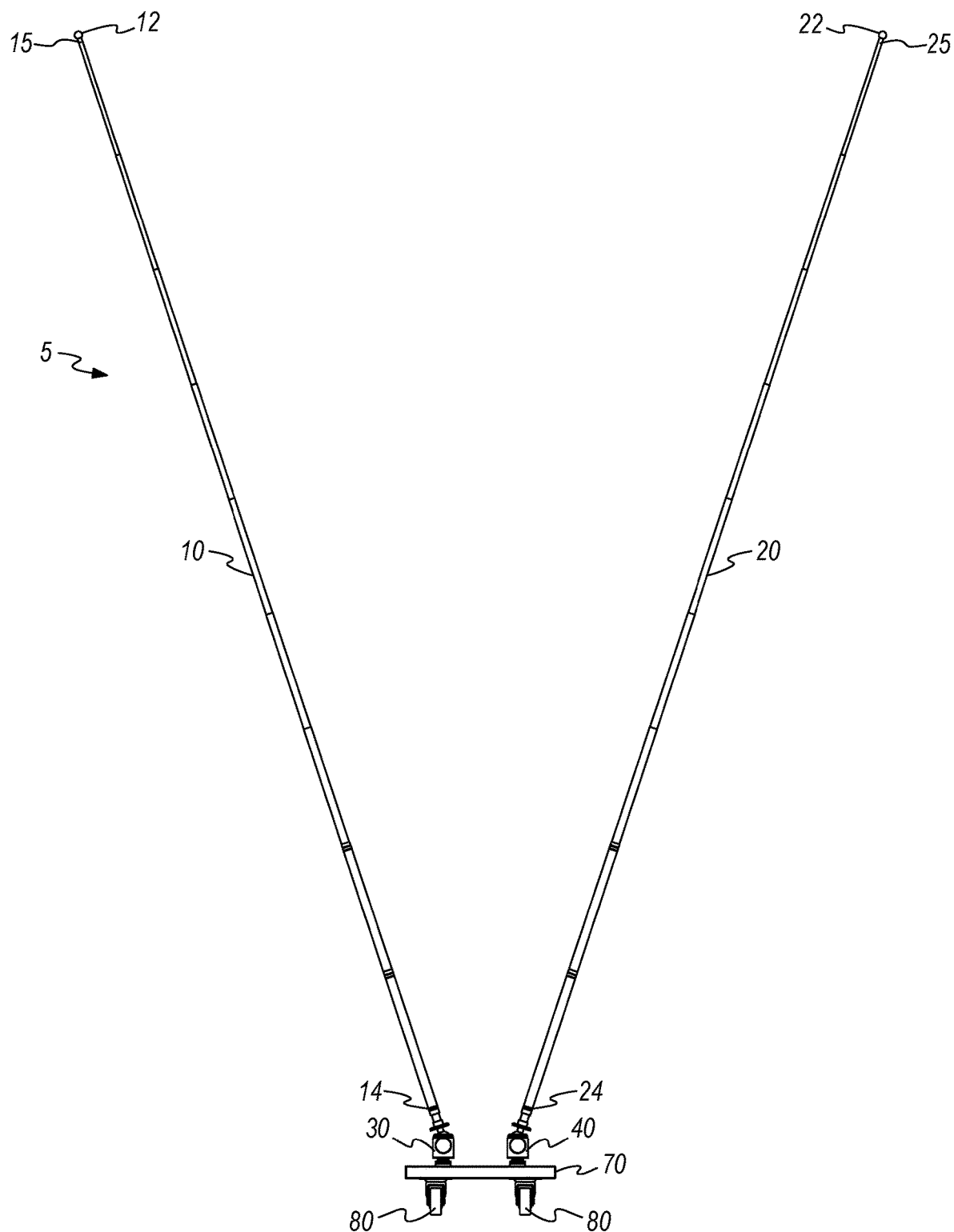
FIG. 6 is a front elevation view of dual telescopic pointer with adjustable ball joints with both telescopic pointers in the extended position.
Figure 7:
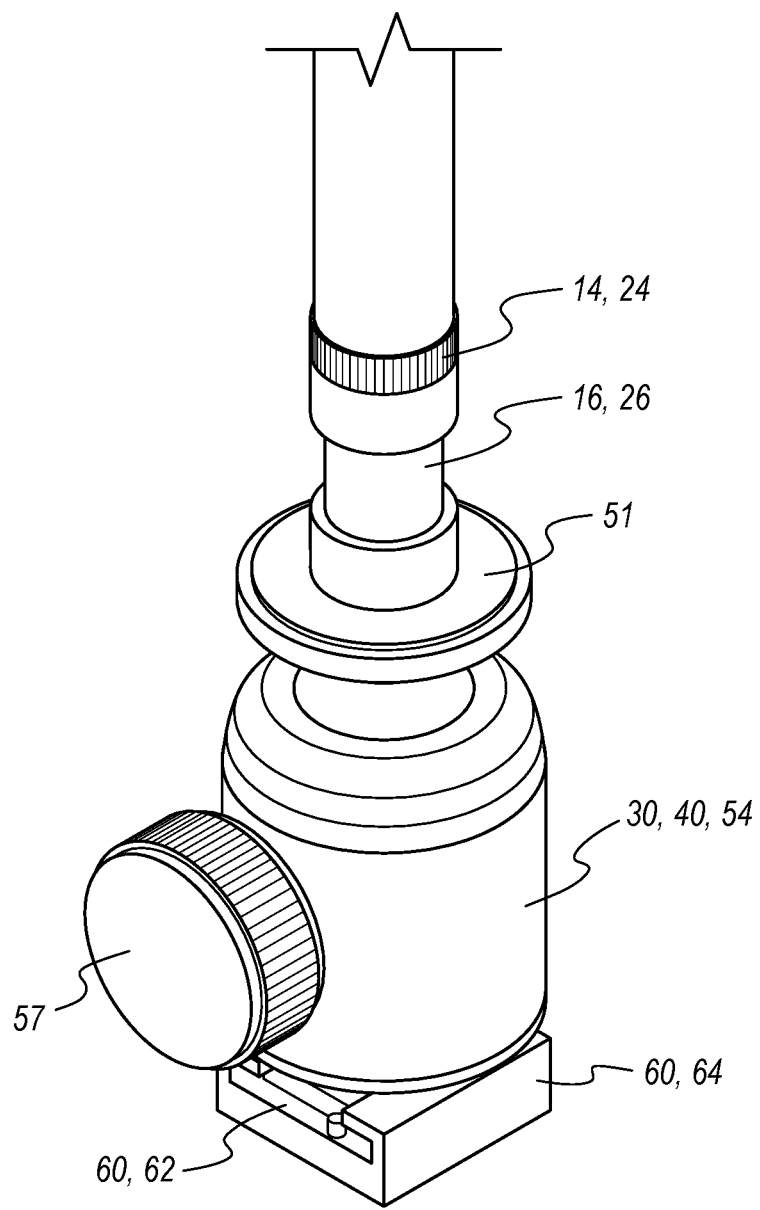
FIG. 7 is an enlarged view of an adjustable ball joint with telescopic pointer attached.

| Term | Definition |
| --- | --- |
| 5 | Dual Telescopic Pointer with Adjustable Ball joints |
| 10 | First Telescopic Pointer |
| 12 | First Focus Sphere |
| 14 | Lower End of First Telescopic Pointer |
| 15 | Upper End of First Telescopic Pointer |
| 16 | First Adapter Nut |
| 20 | Second Telescopic Pointer |
| 22 | Second Focus Sphere |
| 24 | Lower End of Second Telescopic Pointer |
| 25 | Upper End Second of Telescopic Pointer |
| 26 | Second Adapter Nut |
| 30 | First Adjustable Ball joint |
| 40 | Second Adjustable Ball joint |
| 50 | Threaded Stud on Adjustable Ball joint |
| 51 | Nut Flange on Adjustable Ball joint |
| 52 | Stud Shaft on Adjustable Ball joint |
| 53 | Ball on Adjustable Ball joint |
| 54 | Ball Casing on Adjustable Ball joint |
| 55 | Block on Adjustable Ball joint |
| 56 | Tapped Hole on Block |
| 57 | Knob on Adjustable Ball joint |
| 58 | Knob Screw on Adjustable Ball joint |
| 59 | Set Screw on Adjustable Ball joint |
| 60 | Base Bracket |
| 62 | Upper End of Base Bracket |
| 64 | Lower End of Base Bracket |
| 70 | Base |
| 80 | Caster or Wheel |

DETAILED DESCRIPTION OF THE INVENTION

Dual telescopic pointer with adjustable ball joints 5 is used by a trained clinician to help treat a client or patient with a mental illness. The trained clinician places a dual telescopic pointer with adjustable ball joints 5 in front of a client and then counseling or analyzing the client in the usual fashion while also asking the client to focus their eyes and attention on the first or second focus spheres 12,22 while periodically moving the location of the first or second focus spheres 12,22 by extending and/or retracting the first and second telescopic pointers 10,20 and/or adjusting the first or second adjustable ball joints 30,40 as described below. This method of treatment promotes deeper healing in the subcortical areas of the brain where emotions and trauma are stored.

Dual telescopic pointer with adjustable ball joints 5 comprises: a first telescopic pointer 10; a second telescopic pointer 20; a first adjustable ball joint 30; a second adjustable ball joint 40; and a base 70.

First telescopic pointer 10 is a telescoping or extendable pointer. First telescopic pointer 10 comprises a plurality of rigid hollow cylindrical segments that stack together or retract within each other. There is an outer or first rigid hollow cylindrical segment with a first end, a second end, a length, a longitudinal axis, an inner diameter, and an outer diameter. There is a next inner or second rigid hollow cylindrical segment with a first end, a second end, a length, a longitudinal axis, an inner diameter, and an outer diameter. The second rigid hollow cylindrical segment has an outer diameter that forms a slip fit or press fit with the inner diameter of the first rigid hollow cylindrical segment. This allows the second segment to slide inside the first segment in order to be stored, stacked, or retracted. In the retracted position, the first end of the second rigid hollow cylindrical segment is slid all the way inside the first rigid hollow cylindrical segment so that it is adjacent to the first end of the first rigid hollow cylindrical segment. In the extended position, the first end of the second rigid hollow cylindrical segment is extended all the way out so that it is adjacent to the second end of the first rigid hollow cylindrical segment. There is a flair or stop on each end of the first and second segments to prevent the two segments from separating when extending and retracting. There is a next inner or third rigid hollow cylindrical segment with a first end, a second end, a length, a longitudinal axis, an inner diameter, and an outer diameter. The third rigid hollow cylindrical segment has an outer diameter that forms a slip fit or press fit with the inner diameter of the second rigid hollow cylindrical segment. This allows the third segment to slide inside the second segment in order to be stored, stacked, or retracted. In the retracted position, the first end of the third rigid hollow cylindrical segment is slid all the way inside the second rigid hollow cylindrical segment so that it is adjacent to the first end of the second rigid hollow cylindrical segment. In the extended position, the first end of the third rigid hollow cylindrical segment is extended all the way out so that it is adjacent to the second end of the second rigid hollow cylindrical segment. There is a flair or stop on each end of the second and third segments to prevent the two segments from separating when extending and retracting. There is a next inner or fourth rigid hollow cylindrical segment with a first end, a second end, a length, a longitudinal axis, an inner diameter, and an outer diameter. The fourth rigid hollow cylindrical segment has an outer diameter that forms a slip fit or press fit with the inner diameter of the third rigid hollow cylindrical segment. This allows the fourth segment to slide inside the third segment in order to be stored, stacked, or retracted. In the retracted position, the first end of the fourth rigid hollow cylindrical segment is slid all the way inside the third rigid hollow cylindrical segment so that it is adjacent to the first end of the third rigid hollow cylindrical segment. In the extended position, the first end of the fourth rigid hollow cylindrical segment is extended all the way out so that it is adjacent to the second end of the third rigid hollow cylindrical segment. There is a flair or stop on each end of the third and fourth segments to prevent the two segments from separating when extending and retracting. This trend continues with a plurality of additional rigid hollow cylindrical segments that stack or retract inside the previous rigid hollow cylindrical segment. In best mode, first telescopic pointer 10 comprises six segments that stack or retract inside each other.

First telescopic pointer 10 has a lower end 14 and an upper end 15. The lower end 14 of first telescopic pointer 10 is the first end of the first segment of first telescopic pointer 10. The lower end 14 of first telescopic pointer 10 has a male threaded member or female threaded member extending downward therefrom. Male threaded member is a rigid cylindrical member with helical threads on its outer surface. Male threaded member has a length and a longitudinal axis. The longitudinal axis of male threaded member is concentric with that of the first segment of first telescopic pointer 10. Male threaded member forms a closed end on the first end of the first segment of first telescopic pointer 10. Female threaded member is a tapped hole or a hole with female thread running along its inside surface. Female threaded member has a length and a longitudinal axis. The longitudinal axis of female threaded member is concentric with that of the first segment of first telescopic pointer 10. Female threaded member forms an open end on the first end of the first segment of first telescopic pointer 10. The upper end 15 of first telescopic pointer 10 is the second end of the last segment of first telescopic pointer 10. In best mode, the upper end 15 of first telescopic pointer 10 is the second end of the sixth segment of first telescopic pointer 10.

First telescopic pointer 10 further comprises a first focus sphere 12. First focus sphere 12 is a rigid spherical shaped member. First focus sphere 12 is rigidly attached to the upper end 15 of first telescopic pointer 10. First focus sphere 12 functions to attract and retain the attention of the client so that the client focuses their vision and attention directly onto first focus sphere 12. As stated below, the trained clinician may move the first focus sphere 12 during the treatment as the client is focusing on the first focus sphere 12. First focus sphere 12 may be made from any material. In best mode, first focus sphere 12 is chromed or otherwise has an extremely shiny quality.

The lower end 14 of first telescopic pointer 10 is reversibly rigidly attachable to a threaded stud 50 on first adjustable ball joint 30 by a removable threaded connection wherein the lower end 14 of first telescopic pointer 10, female threaded member, may be screwed onto threaded stud 50 on first adjustable ball joint 30 to rigidly connect thereto and unscrewed from threaded stud 50 on first adjustable ball joint 30 to disconnect therefrom. In an alternate embodiment, a first adapter nut 16 may be used for this connection as described below.

First telescopic pointer 10 may further comprise a first adapter nut 16. First adapter nut 16 is a rigid cylindrical member with a first end, a second end, a length, and a longitudinal axis. The second end of first a first adapter nut 16 has a threaded hole or tapped hole thereon. The threaded hole or tapped hole on the second end of first a first adapter nut 16 has a longitudinal axis that is concentric with that of first adapter nut 16. The female threads on the threaded hole or tapped hole on the second end of first adapter nut 16 are sized to engage with the male threaded member on the lower end 14 of first telescopic pointer 10. The lower end 14 of first telescopic pointer 10 is reversibly rigidly attachable to the second end of first adapter nut 16 by a removable threaded connection wherein the lower end 14 of first telescopic pointer 10 may be screwed onto the second end of first a first adapter nut 16 to rigidly connect thereto and unscrewed from the second end of first adapter nut 16 to disconnect therefrom. The first end of first adapter nut 16 has a threaded hole or tapped hole thereon. The threaded hole or tapped hole on the first end of first a first adapter nut 16 has a longitudinal axis that is concentric with that of first adapter nut 16. The female threads on the threaded hole or tapped hole on the first end of first a first adapter nut 16 are sized to engage with a male threaded member or threaded stud 50 on first adjustable ball joint 30. The first end of first adapter nut 16 is reversibly rigidly attachable to a threaded stud 50 on first adjustable ball joint 30 by a removable threaded connection wherein the first end of first adapter nut 16 may be screwed onto threaded stud 50 on first adjustable ball joint 30 to rigidly connect thereto and unscrewed from threaded stud 50 on first adjustable ball joint 30 to disconnect therefrom. The threaded hole or tapped hole on the first end of first adapter nut 16 may have different sizing than the threaded hole or tapped hole on the second end of first adapter nut 16.

First adjustable ball joint 30 is an adjustable ball joint. First adjustable ball joint 30 comprises: a threaded stud 50; a nut flange 51; a stud shaft 52; a ball 53; a ball casing 54; a block 55; a knob 57; a knob screw 58, and a set screw 59. As stated, the lower end 14 of first telescopic pointer 10 may be reversibly rigidly attachable to the threaded stud 50 on first adjustable ball joint 30. Alternately, the lower end 14 of first telescopic pointer 10 may be reversibly rigidly attachable to the second end of first adapter nut 16 and the first end of first adapter nut 16 is reversibly rigidly attachable to the first adjustable ball joint 30, wherein the first end of first adapter nut 16 may be screwed onto to the threaded stud 50 on the first adjustable ball joint 30 to rigidly connect thereto and unscrewed from the threaded stud 50 on the first adjustable ball joint 30 to disconnect therefrom. The first adjustable ball joint 30 is reversibly rigidly attached to the upper surface of base 70 or to a first base bracket 60 and the first base bracket 60 is rigidly attached to the base 70 as described below. First adjustable ball joint 30 functions to adjustably attach first telescopic pointer 10 to base 70 and allow the first telescopic pointer 10 to be adjusted to point in any direction relative to the base 70 and then tightened to retain this position as described below.

Second telescopic pointer 20 is a telescoping or extendable pointer. Second telescopic pointer 20 comprises a plurality of rigid hollow cylindrical segments that stack together or retract within each other. There is an outer or first rigid hollow cylindrical segment with a first end, a second end, a length, a longitudinal axis, an inner diameter, and an outer diameter. There is a next inner or second rigid hollow cylindrical segment with a first end, a second end, a length, a longitudinal axis, an inner diameter, and an outer diameter. The second rigid hollow cylindrical segment has an outer diameter that forms a slip fit or press fit with the inner diameter of the first rigid hollow cylindrical segment. This allows the second segment to slide inside the first segment in order to be stored, stacked, or retracted. In the retracted position, the first end of the second rigid hollow cylindrical segment is slid all the way inside the first rigid hollow cylindrical segment so that it is adjacent to the first end of the first rigid hollow cylindrical segment. In the extended position, the first end of the second rigid hollow cylindrical segment is extended all the way out so that it is adjacent to the second end of the first rigid hollow cylindrical segment. There is a flair or stop on each end of the first and second segments to prevent the two segments from separating when extending and retracting. There is a next inner or third rigid hollow cylindrical segment with a first end, a second end, a length, a longitudinal axis, an inner diameter, and an outer diameter. The third rigid hollow cylindrical segment has an outer diameter that forms a slip fit or press fit with the inner diameter of the second rigid hollow cylindrical segment. This allows the third segment to slide inside the second segment in order to be stored, stacked, or retracted. In the retracted position, the first end of the third rigid hollow cylindrical segment is slid all the way inside the second rigid hollow cylindrical segment so that it is adjacent to the first end of the second rigid hollow cylindrical segment. In the extended position, the first end of the third rigid hollow cylindrical segment is extended all the way out so that it is adjacent to the second end of the second rigid hollow cylindrical segment. There is a flair or stop on each end of the second and third segments to prevent the two segments from separating when extending and retracting. There is a next inner or fourth rigid hollow cylindrical segment with a first end, a second end, a length, a longitudinal axis, an inner diameter, and an outer diameter. The fourth rigid hollow cylindrical segment has an outer diameter that forms a slip fit or press fit with the inner diameter of the third rigid hollow cylindrical segment. This allows the fourth segment to slide inside the third segment in order to be stored, stacked, or retracted. In the retracted position, the first end of the fourth rigid hollow cylindrical segment is slid all the way inside the third rigid hollow cylindrical segment so that it is adjacent to the first end of the third rigid hollow cylindrical segment. In the extended position, the first end of the fourth rigid hollow cylindrical segment is extended all the way out so that it is adjacent to the second end of the third rigid hollow cylindrical segment. There is a flair or stop on each end of the third and fourth segments to prevent the two segments from separating when extending and retracting. This trend continues with a plurality of additional rigid hollow cylindrical segments that stack or retract inside the previous rigid hollow cylindrical segment. In best mode, second telescopic pointer 20 comprises six segments that stack or retract inside each other.

Second telescopic pointer 20 has a lower end 24 and an upper end 25. The lower end 24 of second telescopic pointer 20 is the first end of the first segment of second telescopic pointer 20. The lower end 24 of second telescopic pointer 20 has a male threaded member or female threaded member extending downward therefrom. Male threaded member is a rigid cylindrical member with helical threads on its outer surface. Male threaded member has a length and a longitudinal axis. The longitudinal axis of male threaded member is concentric with that of the first segment of second telescopic pointer 20. Male threaded member forms a closed end on the first end of the first segment of second telescopic pointer 20. Female threaded member is a tapped hole or a hole with female thread running along its inside surface. Female threaded member has a length and a longitudinal axis. The longitudinal axis of female threaded member is concentric with that of the first segment of second telescopic pointer 20. Female threaded member forms an open end on the first end of the second segment of first telescopic pointer 20. The upper end 25 of second telescopic pointer 20 is the second end of the last segment of second telescopic pointer 20. In best mode, the upper end 25 of second telescopic pointer 20 is the second end of the sixth segment of second telescopic pointer 20.

Second telescopic pointer 20 further comprises a second focus sphere 22. Second focus sphere 22 is a rigid spherical shaped member. Second focus sphere 22 is rigidly attached to the upper end 25 of second telescopic pointer 20. Second focus sphere 22 functions to attract and retain the attention of the client so that the client focuses their vision and attention directly onto second focus sphere 22. As stated below, the trained clinician may move the second focus sphere 22 during the treatment as the client is focusing on the second focus sphere 22. Second focus sphere 22 may be made from any material. In best mode, second focus sphere 22 is chromed or otherwise has an extremely shiny quality.

The lower end 24 of second telescopic pointer 20 is reversibly rigidly attachable to a threaded stud 50 on second adjustable ball joint 40 by a removable threaded connection wherein the lower end 24 of second telescopic pointer 20, female threaded member, may be screwed onto threaded stud 50 on second adjustable ball joint 40 to rigidly connect thereto and unscrewed from threaded stud 50 on first adjustable ball joint 30 to disconnect therefrom. In an alternate embodiment, a second adapter nut 26 may be used for this connection as described below.

Second telescopic pointer 20 may further comprise a second adapter nut 26. Second adapter nut 26 is a rigid cylindrical member with a first end, a second end, a length, and a longitudinal axis. The second end of second a first adapter nut 26 has a threaded hole or tapped hole thereon. The threaded hole or tapped hole on the second end of second a first adapter nut 26 has a longitudinal axis that is concentric with that of second adapter nut 26. The female threads on the threaded hole or tapped hole on the second end of second adapter nut 26 are sized to engage with the male threaded member on the lower end 24 of second telescopic pointer 20. The lower end 24 of second telescopic pointer 20 is reversibly rigidly attachable to the second end of second adapter nut 26 by a removable threaded connection wherein the lower end 24 of second telescopic pointer 20 may be screwed onto the second end of first a second adapter nut 26 to rigidly connect thereto and unscrewed from the second end of second adapter nut 26 to disconnect therefrom. The first end of second adapter nut 26 has a threaded hole or tapped hole thereon. The threaded hole or tapped hole on the first end of second a first adapter nut 26 has a longitudinal axis that is concentric with that of second adapter nut 26. The female threads on the threaded hole or tapped hole on the first end of second a first adapter nut 26 are sized to engage with a male threaded member or threaded stud 50 on second adjustable ball joint 40. The first end of second adapter nut 26 is reversibly rigidly attachable to a threaded stud 50 on second adjustable ball joint 40 by a removable threaded connection wherein the first end of second adapter nut 26 may be screwed onto threaded stud 50 on second adjustable ball joint 40 to rigidly connect thereto and unscrewed from threaded stud 50 on second adjustable ball joint 40 to disconnect therefrom. The threaded hole or tapped hole on the first end of second adapter nut 26 may have different sizing than the threaded hole or tapped hole on the second end of second adapter nut 26.

Second adjustable ball joint 40 is an adjustable ball joint. Second adjustable ball joint 40 comprises: a threaded stud 50; a nut flange 51; a stud shaft 52; a ball 53; a ball casing 54; a block 55; a knob 57; a knob screw 58, and a set screw 59. As stated, the lower end 24 of second telescopic pointer 20 may be reversibly rigidly attachable to the threaded stud 50 on second adjustable ball joint 40 to rigidly connect thereto and unscrewed from the threaded stud 50 on the second adjustable ball joint 40 to disconnect therefrom. Alternately, the lower end 24 of second telescopic pointer 20 may be reversibly rigidly attachable to the second end of second adapter nut 26 and the first end of second adapter nut 26 is reversibly rigidly attachable to the second adjustable ball joint 40, wherein the first end of second adapter nut 26 may be screwed onto to the threaded stud 50 on the second adjustable ball joint 40 to rigidly connect thereto and unscrewed from the threaded stud 50 on the second adjustable ball joint 40 to disconnect therefrom. The second adjustable ball joint 40 is reversibly rigidly attached to the upper surface of base 70 or to a second base bracket 60 and the second base bracket 60 is rigidly attached to the base 70 as described below. Second adjustable ball joint 40 functions to adjustably attach second telescopic pointer 20 to base 70 and allow the second telescopic pointer 20 to be adjusted to point in any direction relative to the base 70 and then tightened to retain this position as described below.

As stated, first adjustable ball joint 30 is attached to first telescopic pointer 10 and second adjustable ball joint 40 is attached to second telescopic pointer 20. First and second adjustable ball joints 30 and 40 are identical and are each described in the same way as follows. Threaded stud 50 is a rigid cylindrical member with an upper end, a lower end, an outside diameter, an outer surface, and a longitudinal axis. Threaded stud 50 has male threads cut into its outer surface running the full length of threaded stud 50. Stud shaft 52 is a rigid cylindrical member with an upper end, a lower end, and a longitudinal axis. Ball 53 is a rigid spherical shaped member with an upper end, a lower end, an outside diameter, and an outer surface. The lower end of threaded stud 50 is rigidly attached to the upper end of stud shaft 52 so that the longitudinal axis of threaded stud 50 is concentric with that of stud shaft 52. The outside diameter of threaded stud 50 is less than that of stud shaft 52 to that the upper end of stud shaft 52 forms a shoulder or flange at the connection point with the lower end of threaded stud. The lower end of stud shaft 52 is rigidly attached to the upper end of ball 53. Rigid attachment may be accomplished by any know means such as: weld, glue, epoxy, adhesive, rivets, clips, snaps, pins, or fasteners. In best mode, threaded stud 50, stud shaft 52, and ball 53 are machined from one piece of material so that threaded stud 50, stud shaft 52, and ball 53 are integral with one-piece construction.

Nut flange 51 is a rigid cylindrical member with a tapped center hole, an upper end, a lower end, an outside diameter, an outer surface, and a longitudinal axis. The tapped center hole on nut flange 51 is a tapped hole or a hole with female thread running along its inside surface. Tapped center hole on nut flange 51 has a longitudinal axis that is concentric with that of nut flange 51. Tapped center hole on nut flange 51 is located in the center of nut flange 51 as depicted. The threads on tapped center hole on nut flange 51 are sized to engage with the male threads on threaded stud 50. Nut flange 51 is reversibly rigidly attachable to threaded stud 50 wherein the lower end of nut flange 51 may be screwed onto to the upper end of threaded stud 50 to rigidly connect thereto and unscrewed from the threaded stud 50 to disconnect therefrom.

Nut flange 51 functions to rigidly retain first or second telescopic pointer 10 or 20 onto threaded stud 50. Nut flange 51 is installed onto threaded stud 50 by threading nut flange 51 all the way onto threaded stud 50 so the lower end of nut flange 51 contacts the upper end of stud shaft 52. Then the lower ends 14,24 of first or second telescopic pointer 10 or 20 are each installed onto threaded stud 50 by threading the lower end 14 of the first telescopic pointer 10 and the lower end 24 of the second telescopic pointer 20 onto the threaded stud 50 until the lower ends 14,24 contact the upper end of nut flange 51. Finally, the nut flange 51 is then rotated counter clockwise to unscrew the nut flange 51 until it tightens up onto the lower ends 14,24 to firmly hold first or second telescopic pointer 10 or 20 onto threaded stud 50. This procedure would be conducted on both first and second adjustable ball joints 30 and 40 to firmly attach first and second telescopic pointers 10 and 20 respectively. Thus, the lower ends 14,24 of first or second telescopic pointer 10 or 20 are each reversibly rigidly attachable to the threaded stud 50 on the first and second adjustable ball joints 30,40 respectively.

Ball casing 54 is a rigid casing, cover, or shell that adjustably retains ball 53. Ball 53 is installed and retained within ball casing 54. Ball casing 54, along with block 55, function to receive and adjustably retain or hold ball 53 within ball casing 54. Ball casing 54 is a rigid hollow cylindrical member with open ends. Ball casing 54 has an upper end, a lower end, an inside diameter, an outside diameter, a length, and a longitudinal axis. Ball casing 54 has first and second tapped hole, each running laterally and perpendicular to the longitudinal axis of ball casing 54. First and second tapped holes each have female thread running along the inside surface. First and second tapped holes each run completely through ball casing 54. The female threads on the first tapped hole are sized to engage with a knob screw 58 as described below. The female threads on the second tapped hole are sized to engage with a set screw 59 as described below. Knob screw 58 and set screw 59 function to help retain block 55 inside ball casing 54 as described below. The inside diameter of the upper end of ball casing 54 is smaller than that of the lower end of ball casing 54. The inside diameter of the upper end of ball casing 54 is smaller than the outside diameter of ball 53 and block 55. The inside diameter of the lower end of ball casing 54 is larger than the outside diameter of ball 53 and block 55. This allows the ball 53 to be installed into ball casing 54 from the lower end of ball casing 54 and retained within the upper end of ball casing 54 wherein ball 53 will not fit through the upper end of ball casing 54. Ball 53 is retained within the lower end of ball casing 54 by block 55 as described below.

Block 55 is a solid rigid cylindrical member with an upper end, an upper half, a lower end, a lower half, an outer surface, an outside diameter, a length, and a longitudinal axis. The outside diameter of block 55 is slightly smaller than the inside diameter of ball casing 54 so that block 55 may be inserted into the lower end of ball casing 54 as depicted. The upper end of block 55 has a hemispherical concave area or depression area that functions to receive the lower end of ball 53 wherein the lower end of ball 53 nests within the hemispherical concave area or depression area on the upper end of block 55. There is a groove or channel around the outer surface of block 55 on the upper half of block 55. The groove or channel goes completely around the outer surface of block 55. The groove or channel has a depth, an upper wall, a bottom surface, and a lower wall. The groove or channel functions to receive the inner end of a knob screw 58 and the inner end of a set screw 59 which help retain the block 55 inside of ball casing 54 as described below. The inner ends of screws 58,59 penetrate the groove or channel when installed as depicted to catch therein and prevent block 55 from falling out through the lower end of ball casing 54. The upper wall of the groove or channel is tapered to form an obtuse angle with the bottom surface of the groove or channel. As described below, the inner end of knob screw 58 contacts the upper wall that is tapered so that the block 55 is forced upwards as the knob screw 58 is tightened on the tapered upper wall. The angle of the tapered wall forces the block 55 upwards as the knob screw 58 is tightened. As described below, this action causes the block 55 move upwards to contact the ball 53 in order to tighten the ball 53 against the upper end of ball casing 54, which retains the ball 53 because it has a smaller inside diameter.

Figure 8A:
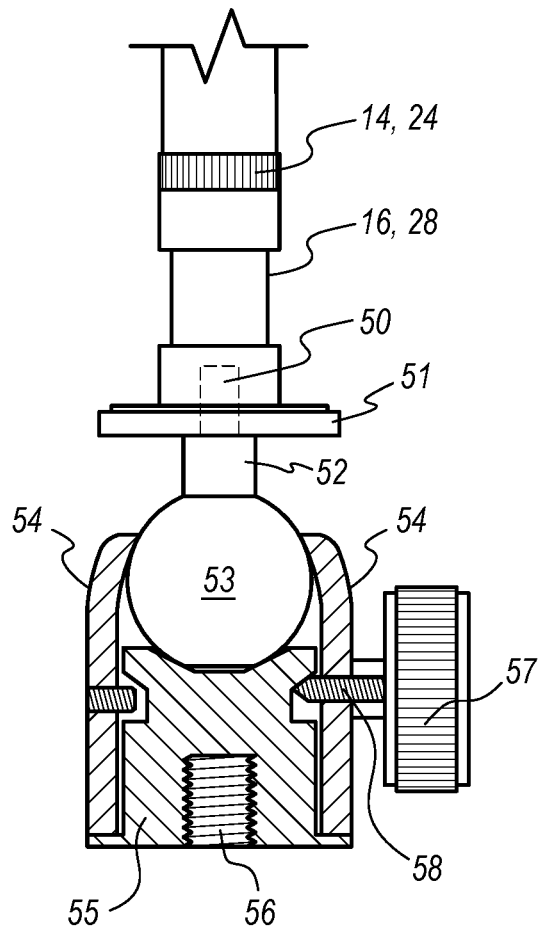
FIG. 8A is cross sectional view of an adjustable ball joint in the tightened position with knob turned clockwise to tighten.
Figure 8B:
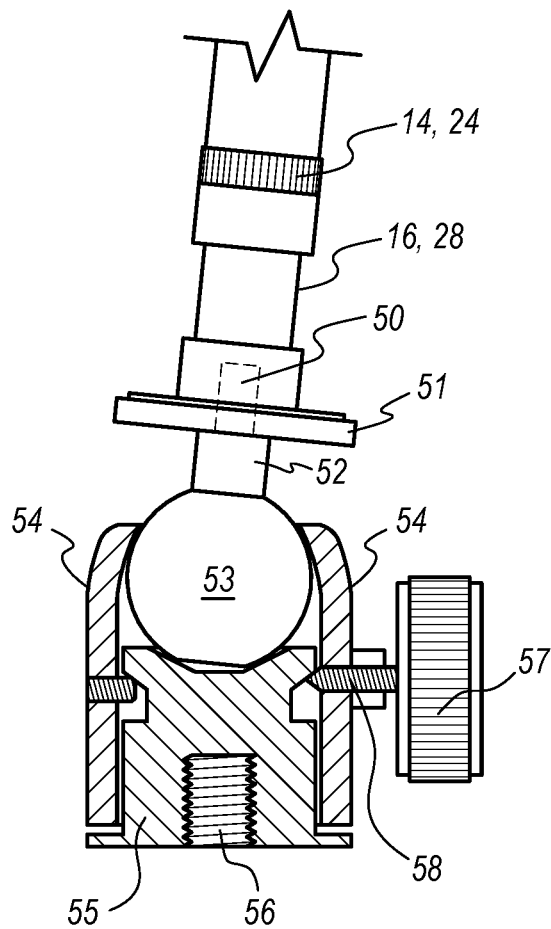
FIG. 8B is cross sectional view of an adjustable ball joint in the loosened position with knob turned counterclockwise to loosen.

This action squeezes ball 53 like a vise to clamp ball 53 and to prevent it from moving as depicted in FIG. 8A. Alternately, when the knob screw 58 is loosened, this allows block 55 to drop downwards thereby unclamping ball 53 and allowing ball 53 to be adjusted or moved as depicted in FIG. 8B. There is a shoulder or flange around the lower end of block 55. The shoulder or flange has an outside diameter that is greater than the inside diameter of ball casing 54 and about equal to the outside diameter of ball casing 54. The shoulder or flange functions to prevent block 55 from being completely inserted into ball casing 54 where the shoulder or flange contacts the lower end of ball casing 54 which acts as stop to prevent complete insertion of block 55 into ball casing 54, as depicted. There is a tapped hole 56 on the lower end of block 55. Tapped hole 56 has a longitudinal axis that is coincident with that of block 55. Tapped hole 56 is a tapped hole or a hole with female thread running along its inside surface. Tapped hole 56 has female thread that is sized to engage with a male threaded member on the upper end 62 of base bracket 60 as described below.

Knob 57 is a knob or rounded protuberance that is used a hand control or switch. Knob 57 has an outer surface, an inner surface, and a longitudinal axis. Knob screw 58 is a screw, bolt, male threaded member, or rigid cylindrical member with helical threads running along its outer surface. Knob screw 58 has an outer end, an inner end, and a longitudinal axis. The outer end of knob screw 58 is rigidly attached to the inner surface of knob 57 with the longitudinal axis of knob screw 58 concentric with that of knob 57. The threads on knob screw 58 are sized to engage with first tapped hole on ball casing 54.

Set screw 59 is a screw, bolt, male threaded member, or rigid cylindrical member with helical threads running along its outer surface. Set screw 59 has an outer end, an inner end, and a longitudinal axis. The threads on set screw 59 are sized to engage with second tapped hole on ball casing 54.

To assemble first and second adjustable ball joints 30,40, ball 53 is inserted into the lower end of ball casing 54. Then block 55 is inserted into the lower end of ball casing 54. Next, set screw 59 is inserted into the second tapped hole on ball casing 54 so that the inner end of set screw 59 penetrates the groove or channel on block 55. Then knob 57 and knob screw 58 are inserted into the first tapped hole on ball casing 54 so that the inner end of knob screw 58 penetrates the groove or channel on block 55.

Base 70 is a rigid planar member with an upper surface and a lower surface. Base 70 may be square, rectangular, circular, triangular, or any shape. In best mode, base 70 is square shaped as depicted. The upper surface of base 70 provides stable structure to support first telescopic pointer 10, second telescopic pointer 20, first adjustable ball joint 30, and second adjustable ball joint 40. Base 70 provides stable structure from which the trained clinician may easily move, arrange, or adjust the first and second focus spheres 12,22 on the ends of first and second telescopic pointers 10,20 during treatment of the client. In optional embodiments, base 70 provides stable structure to support a plurality of casters or wheels attached to the bottom surface as described below.

First and second adjustable ball joints 30,40 are rigidly attached to the upper surface of base 70. Rigid attachment may be accomplished by any known means such as weld, glue, epoxy, adhesive, bolts, screws, rivets, clips, snaps, pins, or fasteners. On method of rigid attachment is with two male threaded members embedded within the upper surface of base 70 wherein each male threaded member protrudes perpendicularly upwards from the upper surface of base 70.

Each male threaded member has threads that are sized to engage with the tapped hole 56 on the lower end of block 55. First and second adjustable ball joints 30,40 are each reversibly rigidly attached to one of the male threaded members by screwing them down onto the male threaded member until tightly attached to the male threaded member.

In alternate embodiments, first adjustable ball joint 30 is rigidly attached to the upper surface of base 70 using a first base bracket 60 and second adjustable ball joint 40 is rigidly attached to the upper surface of base 70 using a second base bracket 60. Dual telescopic pointer with adjustable ball joints 5 may further comprise: a first base bracket 60 and a second base bracket 60.

Each base bracket 60 comprises: an upper end 62 and a lower end 64. Upper end 62 of base bracket 60 comprises: a flat head bolt or screw and flat head nut flange. Flat head bolt or screw is a screw, bolt, male threaded member, or rigid cylindrical member with helical threads running along its outer surface. Flat head bolt or screw has threads on one end and a large flat head on the other end. Flat head bolt or screw has a length and a longitudinal axis. The threads on flat head bolt or screw are sized to engage with the tapped hole 56 on the lower end of block 55. Large flat head is a rigid planar member with a length and/or width that is sized to make a slip fit in the receiver on the lower end 64 of base bracket 60 as described below. Flat head nut flange is a rigid cylindrical member with a tapped center hole, an upper end, a lower end, an outside diameter, an outer surface, and a longitudinal axis. The tapped center hole is a tapped hole or a hole with female thread running along its inside surface. Tapped center hole has a longitudinal axis that is concentric with that of flat head nut flange. Tapped center hole is located in the center of flat head nut flange. The threads on tapped center hole are sized to engage with the threads on flat head bolt or screw. Flat head nut flange is reversibly rigidly attachable to flat head bolt or screw. Flat head nut flange functions to rigidly retain flat head bolt or screw within the received on the lower end 64 of base bracket 60 as described below.

Lower end 64 of base bracket 60 comprises a receiver with one or more screw holes. Receiver is a rigid bracket member with a flat head slot on its upper surface. Flat head slot is a set of two grooves that are spaced apart and sized to receive the large flat head on flat head bolt or screw where the flat head makes a slip fit between the two grooves. Each of the one or more screw holes is a hole for a screw. Receiver is rigidly attached to the upper surface of base 70 by fastening a screw or bolt through one or more screw holes and into the upper surface of base 70 to rigidly attach receiver to base 70. Flat head bolt or screw is reversibly rigidly attached to the receiver by sliding the large flat head on flat head bolt or screw into the flat head slot on the receiver so that the longitudinal axis of flat head bolt or screw is pointing upwards and perpendicular to the plane of base 70. Then the flat head nut flange is threaded onto the flat head bolt or screw and tightened down onto the large flat head of flat head bolt or screw to clamp down and sandwich the large flat head between the receiver and the flat head nut flange to rigidly retain flat head bolt or screw in this position.

First adjustable ball joint 30 is reversibly rigidly attached to first base bracket 60 by threading the tapped hole 56 on first adjustable ball joint 30 onto the flat head bolt or screw on the first base bracket 60. Second adjustable ball joint 40 is reversibly rigidly attached to second base bracket 60 by threading the tapped hole 56 on second adjustable ball joint 40 onto the flat head bolt or screw on the second base bracket 60.

Dual telescopic pointer with adjustable ball joints 5 may further comprise: a plurality of casters or wheels 80. Each caster or wheel 80 is a wheel that is designed to be attached to the bottom of a larger object. A wheel is a circular object that revolves on an axle and is fixed below an object to enable it to move easily over the ground. Each caster or wheel 80 may be a swivel caster that freely rotates 180 degrees. Each caster or wheel 80 is rigidly attached to the lower surface of base 70. Casters or wheels 80 allow the base 70 and the entire dual telescopic pointer with adjustable ball joints 5 to be rolled along the floor for easier movement and positioning of the dual telescopic pointer with adjustable ball joints 5 and the first and second focus spheres 12,22. In best mode, four swivel casters or wheels 80 are attached to the lower surface of base 70 as depicted.

The trained clinician uses dual telescopic pointer with adjustable ball joints 5 by placing it in front of a client or patient and then counseling or analyzing the client in the usual fashion while also asking the client to focus their eyes and attention on the first or second focus spheres 12,22 while periodically moving the location of the first or second focus spheres 12,22 by extending and/or retracting the first and second telescopic pointers 10,20 and/or adjusting the first or second adjustable ball joints 30,40. First and second telescopic pointers 10,20 are extended and retracted by pulling and pushing the focus sphere 12,22 to extend and retract the segments of telescopic pointer 10,20. First and second adjustable ball joints 30,40 are adjusted by: loosening the knob 57 by turning it counterclockwise, then moving or angling the telescopic pointer 10,20 to the desired direction, and tightening the knob 57 by turning it clockwise. These steps are repeated as necessary and decided upon by the trained clinician.

What is claimed is:

1. A dual telescopic pointer with adjustable ball joints comprising: a first telescopic pointer; a second telescopic pointer; a first adjustable ball joint; a second adjustable ball joint; and a base, wherein, said first telescopic pointer is a telescoping or extendable pointer comprising a plurality of rigid hollow cylindrical segments that stack together or retract within each other, said first telescopic pointer has a lower end and an upper end, said first telescopic pointer further comprises a first focus sphere that is a rigid spherical shaped member, said first focus sphere is rigidly attached to said upper end of said first telescopic pointer, said first adjustable ball joint is an adjustable ball joint comprising: a threaded stud; a nut flange; a stud shaft; a ball; a ball casing; a block; a knob; a knob screw, and a set screw, said second telescopic pointer is a telescoping or extendable pointer comprising a plurality of rigid hollow cylindrical segments that stack together or retract within each other, said second telescopic pointer has a lower end and an upper end, said second telescopic pointer further comprises a second focus sphere that is a rigid spherical shaped member, said second focus sphere is rigidly attached to said upper end of said second telescopic pointer, said second adjustable ball joint is an adjustable ball joint comprising: a threaded stud; a nut flange; a stud shaft; a ball; a ball casing; a block; a knob; a knob screw, and a set screw, each said threaded stud on said first and second adjustable ball joints is a rigid cylindrical member with an upper end, a lower end, an outside diameter, an outer surface, and a longitudinal axis, each said threaded stud on said first and second adjustable ball joints has male threads cut into its outer surface running the full length of said threaded stud, each said stud shaft on said first and second adjustable ball joints is a rigid cylindrical member with an upper end, a lower end, and a longitudinal axis, each said ball on said first and second adjustable ball joints is a rigid spherical shaped member with an upper end, a lower end, an outside diameter, and an outer surface, each said lower end of each said threaded stud on said first and second adjustable ball joints is rigidly attached to said upper end of said stud shaft on said first and second adjustable ball joints respectively, each said lower end of each said stud shaft on said first and second adjustable ball joints is rigidly attached to said upper end of said ball on said first and second adjustable ball joints respectively, each said nut flange on said first and second adjustable ball joints is a rigid cylindrical member with a tapped center hole, an upper end, a lower end, an outside diameter, an outer surface, and a longitudinal axis, each said nut flange on said first and second adjustable ball joints is reversibly rigidly attachable to said upper end of said threaded stud on said first and second adjustable ball joints respectively, each said lower end of said first or second telescopic pointers is reversibly rigidly attachable to said upper end of said threaded stud on said first and second adjustable ball joints respectively, each said ball casing on said first and second adjustable ball joints is a rigid casing, cover, or shell that adjustably retains said ball, each said ball casing is a rigid hollow cylindrical member with open ends, each said ball casing has an upper end, a lower end, an inside diameter, an outside diameter, a length, and a longitudinal axis, each said ball casing has first and second tapped hole, each running laterally and perpendicular to said longitudinal axis of said ball casing, each said ball on said first and second adjustable ball joints is installed and retained within said ball casing on said first and second adjustable ball joints respectively, each said block on said first and second adjustable ball joints is a solid rigid cylindrical member with an upper end, an upper half, a lower end, a lower half, an outer surface, an outside diameter, a length, and a longitudinal axis, each said upper end of each said block on said first and second adjustable ball joints has a hemispherical concave area or depression area that functions to receive said lower end of said ball wherein said lower end of said ball nests within said hemispherical concave area or depression area, each said upper end of each said block on said first and second adjustable ball joints has a groove or channel around its said outer surface on its said upper half, each said lower end of said block on said first and second adjustable ball joints has a tapped hole with a longitudinal axis that is coincident with that of said block, each said knob on said first and second adjustable ball joints is a knob or rounded protuberance that is used a hand control or switch, each said knob on said first and second adjustable ball joints has an outer surface, an inner surface, and a longitudinal axis, each said knob screw on said first and second adjustable ball joints is a screw, bolt, male threaded member, or rigid cylindrical member with helical threads running along its outer surface, each said knob screw on said first and second adjustable ball joints has an outer end, an inner end, and a longitudinal axis, each said set screw on said first and second adjustable ball joints is a screw, bolt, male threaded member, or rigid cylindrical member with helical threads running along its outer surface, each said set screw on said first and second adjustable ball joints has an outer end, an inner end, and a longitudinal axis, each said outer end of each said knob screw is rigidly attached to said inner surface of each said knob on said first and second adjustable ball joints respectively, each said set screw on said first and second adjustable ball joints is reversibly rigidly attachable to each said second tapped hole on each said ball casing on said first and second adjustable ball joints respectively, each said knob screw on said first and second adjustable ball joints is reversibly rigidly attachable to each said first tapped hole on each said ball casing on said first and second adjustable ball joints respectively, said base is a rigid planar member with an upper surface and a lower surface, said block on said first adjustable ball joint is reversibly rigidly attachable to said upper surface of said base, said block on said second adjustable ball joint is reversibly rigidly attachable to said upper surface of said base, said lower end of said first telescopic pointer is reversibly rigidly attachable to said upper end of said threaded stud on said first adjustable ball joint, and said lower end of said second telescopic pointer is reversibly rigidly attachable to said upper end of said threaded stud on said second adjustable ball joint.

2. A dual telescopic pointer with adjustable ball joints comprising: a first telescopic pointer; a second telescopic pointer; a first adapter nut; a second adapter nut; a first adjustable ball joint; a second adjustable ball joint; and a base, wherein, said first telescopic pointer is a telescoping or extendable pointer comprising a plurality of rigid hollow cylindrical segments that stack together or retract within each other, said first telescopic pointer has a lower end and an upper end, said first telescopic pointer further comprises a first focus sphere that is a rigid spherical shaped member, said first focus sphere is rigidly attached to said upper end of said first telescopic pointer, said first adjustable ball joint is an adjustable ball joint comprising: a threaded stud; a nut flange; a stud shaft; a ball; a ball casing; a block; a knob; a knob screw, and a set screw, said second telescopic pointer is a telescoping or extendable pointer comprising a plurality of rigid hollow cylindrical segments that stack together or retract within each other, said second telescopic pointer has a lower end and an upper end, said second telescopic pointer further comprises a second focus sphere that is a rigid spherical shaped member, said second focus sphere is rigidly attached to said upper end of said second telescopic pointer, said second adjustable ball joint is an adjustable ball joint comprising: a threaded stud; a nut flange; a stud shaft; a ball; a ball casing; a block; a knob; a knob screw, and a set screw, said first adapter nut that is a rigid cylindrical member with a first end and a second end, wherein said first end has a threaded hole or tapped hole thereon and said second end has a threaded hole or tapped hole thereon, said lower end of said first telescopic pointer is reversibly rigidly attachable to said second end of said first adapter nut, said second adapter nut is a rigid cylindrical member with a first end and a second end, wherein said first end has a threaded hole or tapped hole thereon and said second end has a threaded hole or tapped hole thereon, said lower end of said second telescopic pointer is reversibly rigidly attachable to said second end of said second adapter nut, each said threaded stud on said first and second adjustable ball joints is a rigid cylindrical member with an upper end, a lower end, an outside diameter, an outer surface, and a longitudinal axis, each said threaded stud on said first and second adjustable ball joints has male threads cut into its outer surface running the full length of said threaded stud, each said stud shaft on said first and second adjustable ball joints is a rigid cylindrical member with an upper end, a lower end, and a longitudinal axis, each said ball on said first and second adjustable ball joints is a rigid spherical shaped member with an upper end, a lower end, an outside diameter, and an outer surface, each said lower end of each said threaded stud on said first and second adjustable ball joints is rigidly attached to said upper end of said stud shaft on said first and second adjustable ball joints respectively, each said lower end of each said stud shaft on said first and second adjustable ball joints is rigidly attached to said upper end of said ball on said first and second adjustable ball joints respectively, each said nut flange on said first and second adjustable ball joints is a rigid cylindrical member with a tapped center hole, an upper end, a lower end, an outside diameter, an outer surface, and a longitudinal axis, each said nut flange on said first and second adjustable ball joints is reversibly rigidly attachable to said upper end of said threaded stud on said first and second adjustable ball joints respectively, each said lower end of said first or second telescopic pointers is reversibly rigidly attachable to said upper end of said threaded stud on said first and second adjustable ball joints respectively, each said ball casing on said first and second adjustable ball joints is a rigid casing, cover, or shell that adjustably retains said ball, each said ball casing is a rigid hollow cylindrical member with open ends, each said ball casing has an upper end, a lower end, an inside diameter, an outside diameter, a length, and a longitudinal axis, each said ball casing has first and second tapped hole, each running laterally and perpendicular to said longitudinal axis of said ball casing, each said ball on said first and second adjustable ball joints is installed and retained within said ball casing on said first and second adjustable ball joints respectively, each said block on said first and second adjustable ball joints is a solid rigid cylindrical member with an upper end, an upper half, a lower end, a lower half, an outer surface, an outside diameter, a length, and a longitudinal axis, each said upper end of each said block on said first and second adjustable ball joints has a hemispherical concave area or depression area that functions to receive said lower end of said ball wherein said lower end of said ball nests within said hemispherical concave area or depression area, each said upper end of each said block on said first and second adjustable ball joints has a groove or channel around its said outer surface on its said upper half, each said lower end of said block on said first and second adjustable ball joints has a tapped hole with a longitudinal axis that is coincident with that of said block, each said knob on said first and second adjustable ball joints is a knob or rounded protuberance that is used a hand control or switch, each said knob on said first and second adjustable ball joints has an outer surface, an inner surface, and a longitudinal axis, each said knob screw on said first and second adjustable ball joints is a screw, bolt, male threaded member, or rigid cylindrical member with helical threads running along its outer surface, each said knob screw on said first and second adjustable ball joints has an outer end, an inner end, and a longitudinal axis, each said set screw on said first and second adjustable ball joints is a screw, bolt, male threaded member, or rigid cylindrical member with helical threads running along its outer surface, each said set screw on said first and second adjustable ball joints has an outer end, an inner end, and a longitudinal axis, each said outer end of each said knob screw is rigidly attached to said inner surface of each said knob on said first and second adjustable ball joints respectively, each said set screw on said first and second adjustable ball joints is reversibly rigidly attachable to each said second tapped hole on each said ball casing on said first and second adjustable ball joints respectively, each said knob screw on said first and second adjustable ball joints is reversibly rigidly attachable to each said first tapped hole on each said ball casing on said first and second adjustable ball joints respectively, said first end of said first adapter nut is reversibly rigidly attachable to said upper end of said threaded stud on said first adjustable ball joint, said first end of said second adapter nut is reversibly rigidly attachable to said upper end of said threaded stud on said second adjustable ball joint, said base is a rigid planar member with an upper surface and a lower surface, said block on said first adjustable ball joint is reversibly rigidly attachable to said upper surface of said base, and said block on said second adjustable ball joint is reversibly rigidly attachable to said upper surface of said base.

3. A dual telescopic pointer with adjustable ball joints comprising: a first telescopic pointer; a second telescopic pointer; a first adapter nut; a second adapter nut; a first adjustable ball joint; a second adjustable ball joint; a first base bracket; a second base bracket; and a base, wherein, said first telescopic pointer is a telescoping or extendable pointer comprising a plurality of rigid hollow cylindrical segments that stack together or retract within each other, said first telescopic pointer has a lower end and an upper end, said first telescopic pointer further comprises a first focus sphere that is a rigid spherical shaped member, said first focus sphere is rigidly attached to said upper end of said first telescopic pointer, said first adjustable ball joint is an adjustable ball joint comprising: a threaded stud; a nut flange; a stud shaft; a ball; a ball casing; a block; a knob; a knob screw, and a set screw, said second telescopic pointer is a telescoping or extendable pointer comprising a plurality of rigid hollow cylindrical segments that stack together or retract within each other, said second telescopic pointer has a lower end and an upper end, said second telescopic pointer further comprises a second focus sphere that is a rigid spherical shaped member, said second focus sphere is rigidly attached to said upper end of said second telescopic pointer, said second adjustable ball joint is an adjustable ball joint comprising: a threaded stud; a nut flange; a stud shaft; a ball; a ball casing; a block; a knob; a knob screw, and a set screw, said first adapter nut that is a rigid cylindrical member with a first end and a second end, wherein said first end has a threaded hole or tapped hole thereon and said second end has a threaded hole or tapped hole thereon, said lower end of said first telescopic pointer is reversibly rigidly attachable to said second end of said first adapter nut, said second adapter nut is a rigid cylindrical member with a first end and a second end, wherein said first end has a threaded hole or tapped hole thereon and said second end has a threaded hole or tapped hole thereon, said lower end of said second telescopic pointer is reversibly rigidly attachable to said second end of said second adapter nut, each said threaded stud on said first and second adjustable ball joints is a rigid cylindrical member with an upper end, a lower end, an outside diameter, an outer surface, and a longitudinal axis, each said threaded stud on said first and second adjustable ball joints has male threads cut into its outer surface running the full length of said threaded stud, each said stud shaft on said first and second adjustable ball joints is a rigid cylindrical member with an upper end, a lower end, and a longitudinal axis, each said ball on said first and second adjustable ball joints is a rigid spherical shaped member with an upper end, a lower end, an outside diameter, and an outer surface, each said lower end of each said threaded stud on said first and second adjustable ball joints is rigidly attached to said upper end of said stud shaft on said first and second adjustable ball joints respectively, each said lower end of each said stud shaft on said first and second adjustable ball joints is rigidly attached to said upper end of said ball on said first and second adjustable ball joints respectively, each said nut flange on said first and second adjustable ball joints is a rigid cylindrical member with a tapped center hole, an upper end, a lower end, an outside diameter, an outer surface, and a longitudinal axis, each said nut flange on said first and second adjustable ball joints is reversibly rigidly attachable to said upper end of said threaded stud on said first and second adjustable ball joints respectively, each said lower end of said first or second telescopic pointers is reversibly rigidly attachable to said upper end of said threaded stud on said first and second adjustable ball joints respectively, each said ball casing on said first and second adjustable ball joints is a rigid casing, cover, or shell that adjustably retains said ball, each said ball casing is a rigid hollow cylindrical member with open ends, each said ball casing has an upper end, a lower end, an inside diameter, an outside diameter, a length, and a longitudinal axis, each said ball casing has first and second tapped hole, each running laterally and perpendicular to said longitudinal axis of said ball casing, each said ball on said first and second adjustable ball joints is installed and retained within said ball casing on said first and second adjustable ball joints respectively, each said block on said first and second adjustable ball joints is a solid rigid cylindrical member with an upper end, an upper half, a lower end, a lower half, an outer surface, an outside diameter, a length, and a longitudinal axis, each said upper end of each said block on said first and second adjustable ball joints has a hemispherical concave area or depression area that functions to receive said lower end of said ball wherein said lower end of said ball nests within said hemispherical concave area or depression area, each said upper end of each said block on said first and second adjustable ball joints has a groove or channel around its said outer surface on its said upper half, each said lower end of said block on said first and second adjustable ball joints has a tapped hole with a longitudinal axis that is coincident with that of said block, each said knob on said first and second adjustable ball joints is a knob or rounded protuberance that is used a hand control or switch, each said knob on said first and second adjustable ball joints has an outer surface, an inner surface, and a longitudinal axis, each said knob screw on said first and second adjustable ball joints is a screw, bolt, male threaded member, or rigid cylindrical member with helical threads running along its outer surface, each said knob screw on said first and second adjustable ball joints has an outer end, an inner end, and a longitudinal axis, each said set screw on said first and second adjustable ball joints is a screw, bolt, male threaded member, or rigid cylindrical member with helical threads running along its outer surface, each said set screw on said first and second adjustable ball joints has an outer end, an inner end, and a longitudinal axis, each said outer end of each said knob screw is rigidly attached to said inner surface of each said knob on said first and second adjustable ball joints respectively, each said set screw on said first and second adjustable ball joints is reversibly rigidly attachable to each said second tapped hole on each said ball casing on said first and second adjustable ball joints respectively, each said knob screw on said first and second adjustable ball joints is reversibly rigidly attachable to each said first tapped hole on each said ball casing on said first and second adjustable ball joints respectively, said first end of said first adapter nut is reversibly rigidly attachable to said upper end of said threaded stud on said first adjustable ball joint, said first end of said second adapter nut is reversibly rigidly attachable to said upper end of said threaded stud on said second adjustable ball joint, each said first and second base bracket comprises: an upper end and a lower end, each said upper end of said first and second of base brackets comprises: a flat head bolt or screw and flat head nut flange, each said flat head bolt or screw is a screw, bolt, male threaded member, or rigid cylindrical member with helical threads running along its outer surface with a large flat head on one end, each said flat head nut flange is a rigid cylindrical member with a tapped center hole, an upper end, a lower end, an outside diameter, an outer surface, and a longitudinal axis, each said lower end of said first and second of base brackets comprises a receiver with one or more screw holes, each said receiver is a rigid bracket member with a flat head slot on its upper surface, each said flat head slot is a set of two grooves that are spaces apart or sized to receive said large flat head on said flat head bolt or screw, each said one or more screw holes is a hole for a screw, said base is a rigid planar member with an upper surface and a lower surface, each said receiver is rigidly attached to said upper surface of said base by fastening a screw or bolt through said one or more screw holes and into said upper surface of said base, each said flat head bolt or screw is reversibly rigidly attached to said receiver by sliding said large flat head on said flat head bolt or screw into said flat head slot on said receiver, each said flat head nut flange is reversibly rigidly attachable to said flat head bolt or screw, said tapped hole on said first adjustable ball joint is reversibly rigidly attached to said flat head bolt or screw on said first base bracket, and said tapped hole on said second adjustable ball joint is reversibly rigidly attached to said flat head bolt or screw on said second base bracket.

* * * * *